United States Patent
Koch et al.

(10) Patent No.: US 8,423,174 B2
(45) Date of Patent: Apr. 16, 2013

(54) METHOD AND LABORATORY SYSTEM FOR HANDLING SAMPLE TUBE RACKS

(75) Inventors: Bruno Koch, Steinhausen (CH);
Markus Kurmann, Nottwil (CH);
Marcel Lustenberger, Eschenbach (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 693 days.

(21) Appl. No.: 12/460,821

(22) Filed: Jul. 23, 2009

(65) Prior Publication Data

US 2010/0049358 A1 Feb. 25, 2010

(30) Foreign Application Priority Data

Jul. 25, 2008 (EP) .................................. 08013460

(51) Int. Cl.
*G06F 7/00* (2006.01)
(52) U.S. Cl.
USPC ... 700/214; 414/791.6; 414/267; 414/331.05; 414/281; 221/9
(58) Field of Classification Search .................. 700/214
See application file for complete search history.

(56) References Cited

U.S. PATENT DOCUMENTS

| | | | | |
|---|---|---|---|---|
| 4,911,602 A * | 3/1990 | Abe | ............... | 414/421 |
| 5,056,437 A | 10/1991 | Maddock | ................. | 104/88.03 |
| 5,143,193 A * | 9/1992 | Geraci | ............... | 194/212 |
| 5,721,384 A | 2/1998 | Tanihati | ................. | 73/864.81 |
| 5,985,215 A | 11/1999 | Sakazume et al. | ............... | 422/67 |
| 6,068,437 A | 5/2000 | Boje et al. | ................. | 414/331.02 |
| 6,129,428 A | 10/2000 | Helwig et al. | ................. | 312/114 |
| 6,220,451 B1 | 4/2001 | Hoffmann | ................. | 209/522 |
| 6,478,524 B1 | 11/2002 | Malin | ............... | 414/283 |
| 6,588,625 B2 * | 7/2003 | Luoma et al. | ................. | 221/9 |
| 6,599,476 B1 | 7/2003 | Watson et al. | ................. | 422/63 |
| 6,926,058 B2 | 8/2005 | Sato et al. | ................. | 156/556 |
| 7,214,023 B2 * | 5/2007 | Sato et al. | ................. | 414/281 |
| 7,314,341 B2 | 1/2008 | Malin | ................. | 414/331.02 |
| 7,364,907 B2 | 4/2008 | Weselak et al. | ................. | 436/43 |
| 8,176,747 B2 * | 5/2012 | Howard et al. | ................. | 62/378 |

(Continued)

FOREIGN PATENT DOCUMENTS

| | | |
|---|---|---|
| DE | 102004058216 | 6/2006 |
| EP | 0 467 302 | 1/1992 |

(Continued)

OTHER PUBLICATIONS

Handbook of Clinical Automation, Robotics and Optimization, G. Kost ed., Chapters 12 and 13, Wiley & Sons, Inc. (1996).

(Continued)

*Primary Examiner* — Gene Crawford
*Assistant Examiner* — Kyle Logan
(74) *Attorney, Agent, or Firm* — McDonnell Boehnen Hulbert & Berghoff LLP

(57) ABSTRACT

A method and laboratory system for handling sample tube racks are disclosed. The laboratory system includes a storage section (14) with a plurality of shelves (110) for storing a plurality of storage racks (SR), a disposal unit (18) for disposing sample tubes from the storage racks (SR), a robotic transfer system (510) for loading storage racks (SR) into the storage section (14), for retrieving storage racks (SR) from the storing section (14) and for bringing storage rack to the disposal unit (18) after a given storage time has elapsed.

13 Claims, 11 Drawing Sheets

U.S. PATENT DOCUMENTS

| | | | |
|---|---|---|---|
| 2002/0023444 A1 | 2/2002 | Felder et al. | 62/177 |
| 2004/0213651 A1* | 10/2004 | Malin | 414/331.05 |
| 2005/0053454 A1 | 3/2005 | Wiggli et al. | 414/752.1 |
| 2006/0013730 A1 | 1/2006 | Pollock et al. | 422/63 |
| 2006/0045674 A1 | 3/2006 | Craven | 414/277 |
| 2007/0014469 A1 | 1/2007 | Paillet et al. | 382/159 |
| 2007/0172396 A1* | 7/2007 | Neeper et al. | 422/104 |
| 2008/0044262 A1 | 2/2008 | Kim et al. | |
| 2008/0118338 A1 | 5/2008 | Huang et al. | 414/744.3 |
| 2008/0201012 A1* | 8/2008 | Hoshino | 700/218 |
| 2008/0213080 A1* | 9/2008 | Cachelin et al. | 414/791.6 |
| 2009/0003981 A1* | 1/2009 | Miller | 414/267 |

FOREIGN PATENT DOCUMENTS

| | | |
|---|---|---|
| EP | 1348965 | 10/2003 |
| EP | 1353183 | 10/2003 |
| EP | 1391401 | 2/2004 |
| EP | 1391402 | 2/2004 |
| EP | 1737031 | 12/2006 |
| FR | 2788042 | 7/2000 |
| JP | 9211005 A | 8/1997 |
| JP | 2000118616 A | 4/2000 |
| JP | 2002002909 | 1/2002 |
| JP | 2007161453 | 6/2007 |
| WO | 83/00393 | 3/1983 |
| WO | WO95/05590 | 2/1995 |
| WO | WO99/28724 | 6/1999 |
| WO | WO2009/077465 | 6/2009 |

OTHER PUBLICATIONS

Partial European Search Report dated Nov. 6, 2009 in EP 09 009 330.3.

Extended European Search Report dated Apr. 3, 2009 in EP 08 01 3460.

\* cited by examiner

METHOD AND LABORATORY SYSTEM FOR HANDLING SAMPLE TUBE RACKS

TECHNICAL FIELD

The present invention relates to the handling of sample tube racks in a test laboratory environment, and particularly to a laboratory device for handling sample tube racks in the context of storing such sample tubes in a storage compartment. More particularly, the present invention relates to a laboratory system having a storage section having shelves for storing sample tube racks, a disposal unit for disposing of sample tubes from the racks, and robotic transfer mechanism for loading and retrieving the racks into and out of the storage section.

DESCRIPTION OF THE RELATED ART

In laboratories, such as for example clinical laboratories in which patient samples are examined and submitted to various in-vitro diagnosis tests, test tubes containing samples (such as blood, urine, etc.) have to be handled in high number and in a cautious but still efficient manner. For years now, automated procedures with corresponding systems and devices have been used in this context.

One aspect during the handling of these sample tubes relates to the tubes being placed in a storage compartment which can be, for example, a refrigerating device. For efficient handling purposes, the tubes are not handled individually but placed in so-called racks. Usually, the tubes are placed in special storage racks, which storage racks are then placed into storage compartments such as shelves in the storage device for a predefined time. During this time frame, racks may have to be retrieved by the rack handling device, e.g., in order to deliver a sample tube (which is contained on that rack) in response to a request for further analysis, and subsequently be placed back into storage.

U.S. Pat. No. 7,314,341 discloses a storage system which has a cabinet with controlled climatic conditions, and ring-shaped holders to store the samples within its interior. An automatic transport system moves the samples, with a mechanism to load and unload them within the sample holders. The loading/unloading mechanism and/or the sample holders rotate around a centre axis. The samples are inserted and removed over the top of the assembly by a telescopic mechanism, with a vertical lift column and a transfer guide with a relative vertical movement at the lift trolley through a lock at the upper cover.

U.S. Pat. No. 6,129,428 discloses an object storage device which is a carousel and holds objects in object carriers. They lie only partially on a structure of the object storage device and can be lifted up. The storage station has a carousel-like object storage device and a transport device with an element for holding the object carriers which moves the object carriers parallel and perpendicular to the axis of the carousel-like object storage device. The climatic test cabinet has a window and a storage station inside it consisting of an object storage device and a transport device, which transports one of the object carriers at a time back and forth between the object storage device and the vicinity of the window.

U.S. Pat. No. 6,478,524 discloses a storage arrangement and a storage receptacle for objects, wherein the storage arrangement has a storage device with at least one storage shaft containing several storage spaces arranged on top of each other, and a delivery device for the short-term reception of the objects. The storage arrangement furthermore has a transport device with an object carrier, and has a vertical displacement device, a horizontal rotating device and a horizontal displacement device for displacing the object carrier between the delivery device and the storage spaces. The objects always take up the same angle in respect to the vertical line, wherein a base surface of the objects is preferably horizontally oriented. The storage receptacle consists of a storage cabinet and an integrated storage arrangement. The storage cabinet has a lock window opening, whose dimensions correspond to the dimensions of an object. The delivery device is located outside the storage cabinet.

SUMMARY

The present invention provides a laboratory system to handle sample tube racks, as well as a method for operating a storage section and its associated robotic transfer system for loading sample tube racks into and out of the storage section. In one aspect, a laboratory system for handling laboratory sample tube racks comprises a storage section with a plurality of shelves for storing a plurality of said racks, a disposal unit for disposing sample tubes from the racks, and a robotic transfer system for loading the racks into the storage section, for retrieving the racks from the storing section and for bringing the racks to the disposal unit after a given storage time has elapsed.

According to one embodiment, the robotic transfer system comprises a coupling element for coupling with the sample tube rack to be conveyed, the coupling element transferring push/pull forces on the rack when coupled thereto. The robotic transfer system further comprises a platform for carrying the rack to be conveyed, the platform being operatively connected with a height adjustment device. In case a rack is pulled onto the platform from a storing position, e.g., on a shelf in the storage device, the height adjustment device lowers the platform slightly below the level of the storage position from which the rack is pulled. In case a rack is pushed from the platform in a storing position, e.g., onto a shelf in the storage device, the height adjustment device raises the platform slightly above the level of the storage position into which the rack is pushed.

Thus, the level of the storage handler platform is adjusted depending on the direction in which the rack is handled, thereby allowing for proper insertion and retraction/retrieval of the racks.

In another aspect, a laboratory system is provided to handle laboratory sample tube racks after expiration of a predefined time limit of storing. According to another embodiment, the disposal unit comprises a tilt module with a rack park position positioned above a waste container. The tilt module is designed to tilt over the rack park position when loaded with a rack by the conveying system such that sample tubes contained in the rack fall or slide into the waste container below.

In operation, a rack containing sample tubes to be disposed is placed into the tilt module. Following tilting over of the rack park position, the sample tubes fall out of the rack due to gravity and into the waste container below. This allows for automated disposal of tubes, ensuring that no tubes fall next to the waste container. A deflector or baffle plate may be positioned between the tilt module and the waste container for guiding falling sample into the waste container. After the rack has been emptied, it is brought back into a regular (non-tilted) position and retrieved by the conveying system. During retraction, a sensor may detect whether any tube has remained in the rack. The delivering/retrieving mechanism carried out by the conveying system with respect to the tilting module can be the same or similar to that carried out with respect to a storing position.

Further features and embodiments will become apparent from the description and the accompanying drawings.

It will be understood that the features mentioned above and those described hereinafter can be used not only in the combination specified but also in other combinations or on their own, without departing from the scope of the present disclosure. The disclosure of the invention also covers the corresponding methods of operation of the disclosed devices and systems.

Various implementations are schematically illustrated in the drawings by means of an embodiment by way of example and are hereinafter explained in detail with reference to the drawings. It is understood that the description is in no way limiting on the scope of the present disclosure and is merely an illustration of a typical embodiment.

DETAILED DESCRIPTION

Reference will now be made in detail to some embodiments, examples of which are illustrated in the accompanying drawings. Wherever possible, the same reference numbers are used throughout the drawings to refer to the same or like parts.

Figure 1:
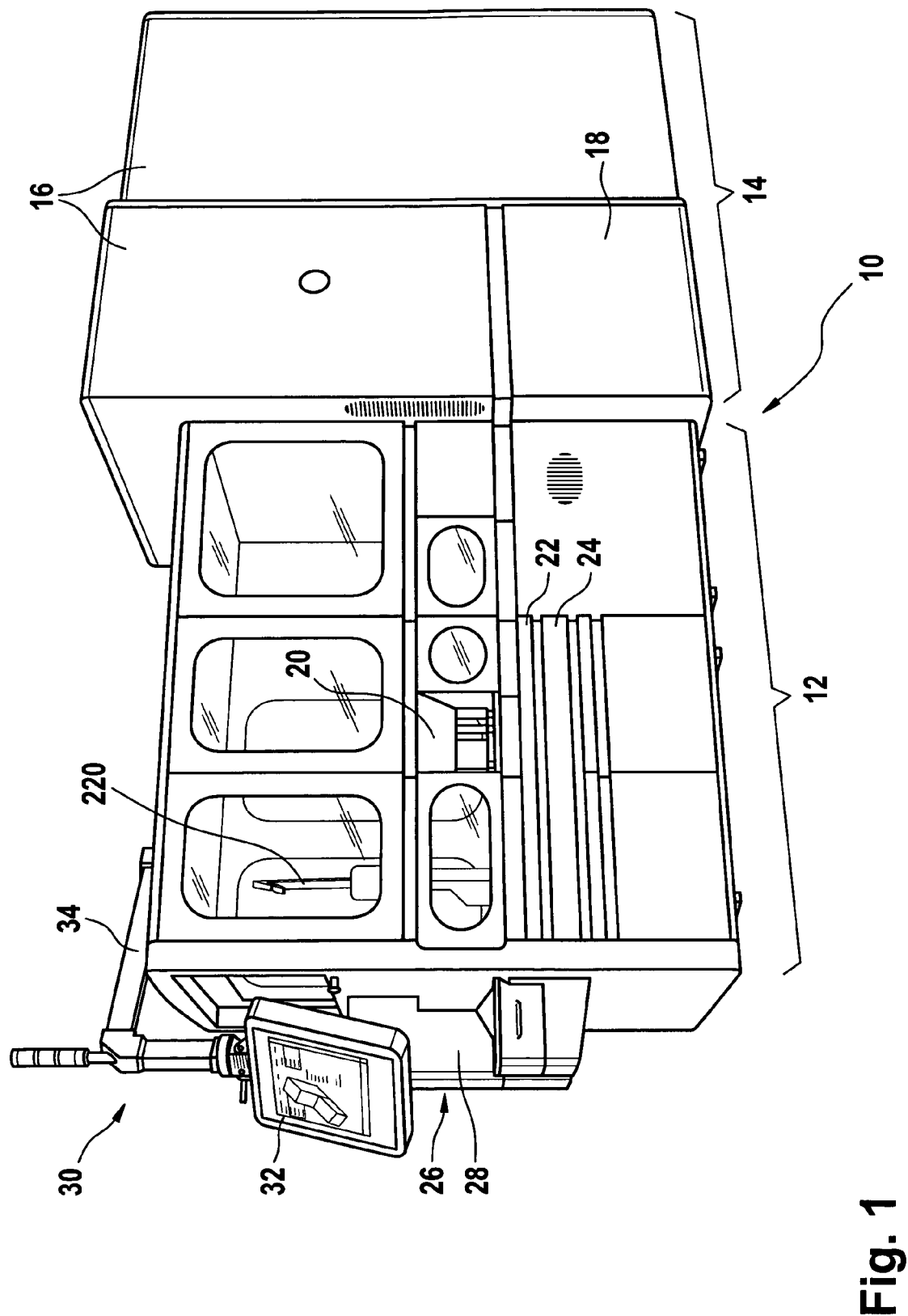
FIG. 1 shows a perspective view of a laboratory equipment unit comprising a laboratory system of the invention.

FIG. 1 shows a perspective view of a laboratory equipment unit 10 comprising a laboratory system in which the invention can be practiced. This laboratory equipment unit 10 may be a so-called storage retrieval module (SRM) forming part of an overall laboratory analyzer system. The storage retrieval module comprises a rack handler section 12 (on the left hand side of the depiction of FIG. 1) and a refrigerating or storage section 14 (on the right hand side of the depiction of FIG. 1). Between the two sections 12, 14 there is a loading/unloading interface (not shown) through which racks are transferred from the rack handler section 12 into the storage section 14 and back (in case of retrieval). This loading/unloading interface may be designed like a gate or the like.

The storage section 14 may comprise a refrigerator 16. A storage section in the context of this invention is a cabinet of various size which is able to store a plurality of sample tubes, preferably in storage racks. It may have an appropriate cooling unit to hold the ambient temperature for the tubes within the refrigerator below room temperature, possibly below 18° C. and possibly below 10° C.

Figure 8:
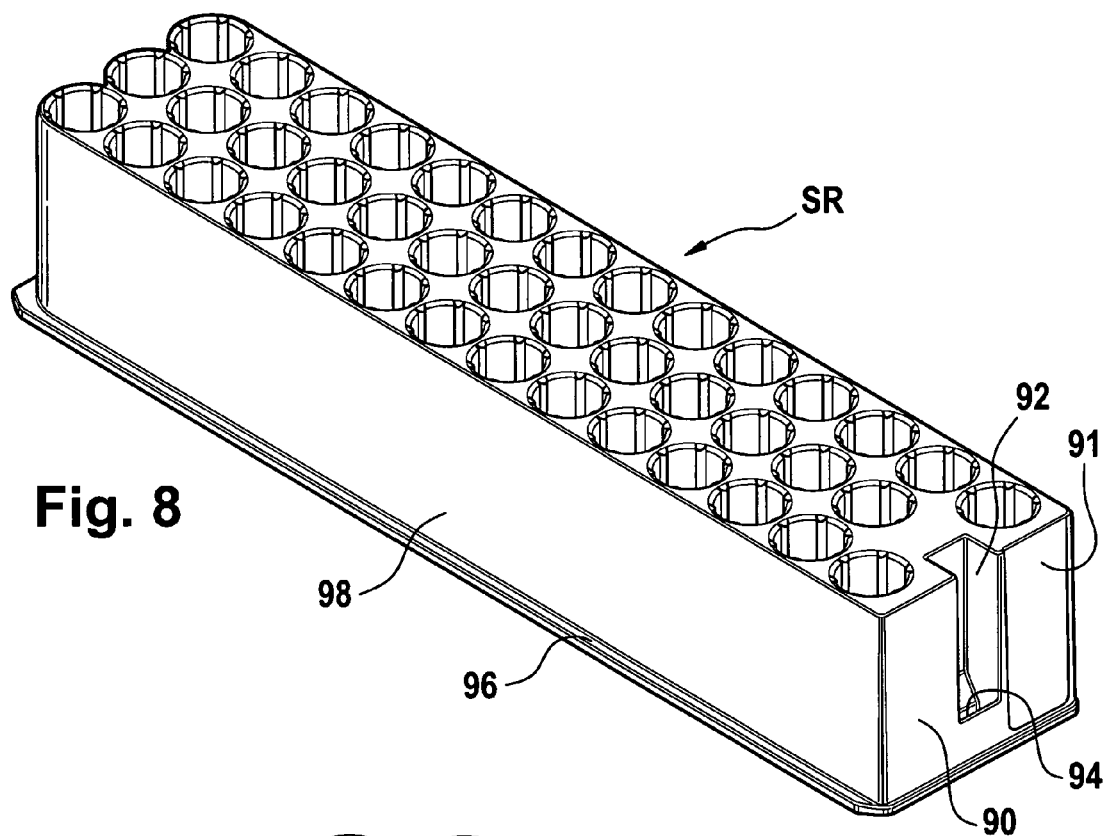
FIG. 8 shows a perspective view of a storage rack.

In its inside, the storage section 14 comprises a plurality of shelves for storage of a high number of sample tube racks. The sample tube racks loaded into the storage section are so-called storage racks (SR), see FIGS. 3 and 8. This implies that all tubes contained in primary racks (i.e., incoming sample tube racks of various types) fulfilling the geometry criteria of the invention are taken out of their respective primary racks and are resorted in suitable storage racks before being loaded into the storage section 14. The storage section may be large enough for one or two human beings being able to enter the inside of the storage section 14 through a door (not shown). In case the door is opened, a safety switching circuit ensures that all moving systems (like robotic arms or other transfer or conveying systems) come to a standstill, for example in a neutral or home position. While primary racks are single-row racks with somewhat standard geometry and therefore designed to be handled in a plurality of different laboratory systems, the secondary sample tube racks (i.e., storage racks) are multi-row racks (e.g., three rows with more than ten positions, for example 13 to 14 positions). Therefore, the storage racks are more stable, particularly for storing purposes, and less likely to tilt over.

Further, the storage section 14 comprises a disposal unit 18. The disposal unit 18 is connected with the storage section 14 via an internal opening (not shown) in a wall separating the storage section 14 from the disposal unit 18. Through this opening, sample tubes whose expiration date (i.e., shelf life) has elapsed can be disposed automatically through the disposal unit 18.

The rack handler section 12 has a housing consisting of several outer walls with windows so that operating personnel can have a direct visual overview of the rack handler's functioning. The rack handler section 12 comprises an opening 20 in one of the outer walls through which primary racks can be inserted into the storage retrieval module 10. The opening 20 leads to a primary rack handler area 210 (cf., FIG. 2) which comprises at least one robotic arm 220 (which can be seen in the depiction of FIG. 1 through one of the windows). The opening 20 might be closable by means of a sliding or retractable door (not shown).

The rack handler section 12 further comprises drawers 22, 24 through which emptied primary racks and/or primary racks containing sample tubes with error designations and/or racks containing at least one retrieved sample tube can be taken out of the storage retrieval module 10.

Further, the rack handler section 12 comprises a capping station 26 with a feeder tank 28 for tube caps.

The storage retrieval module 10 also comprises a man-machine interface (MMI) 30 which might have the form of a touch screen monitor 32 at the end of an articulated arm 34.

Figure 2:
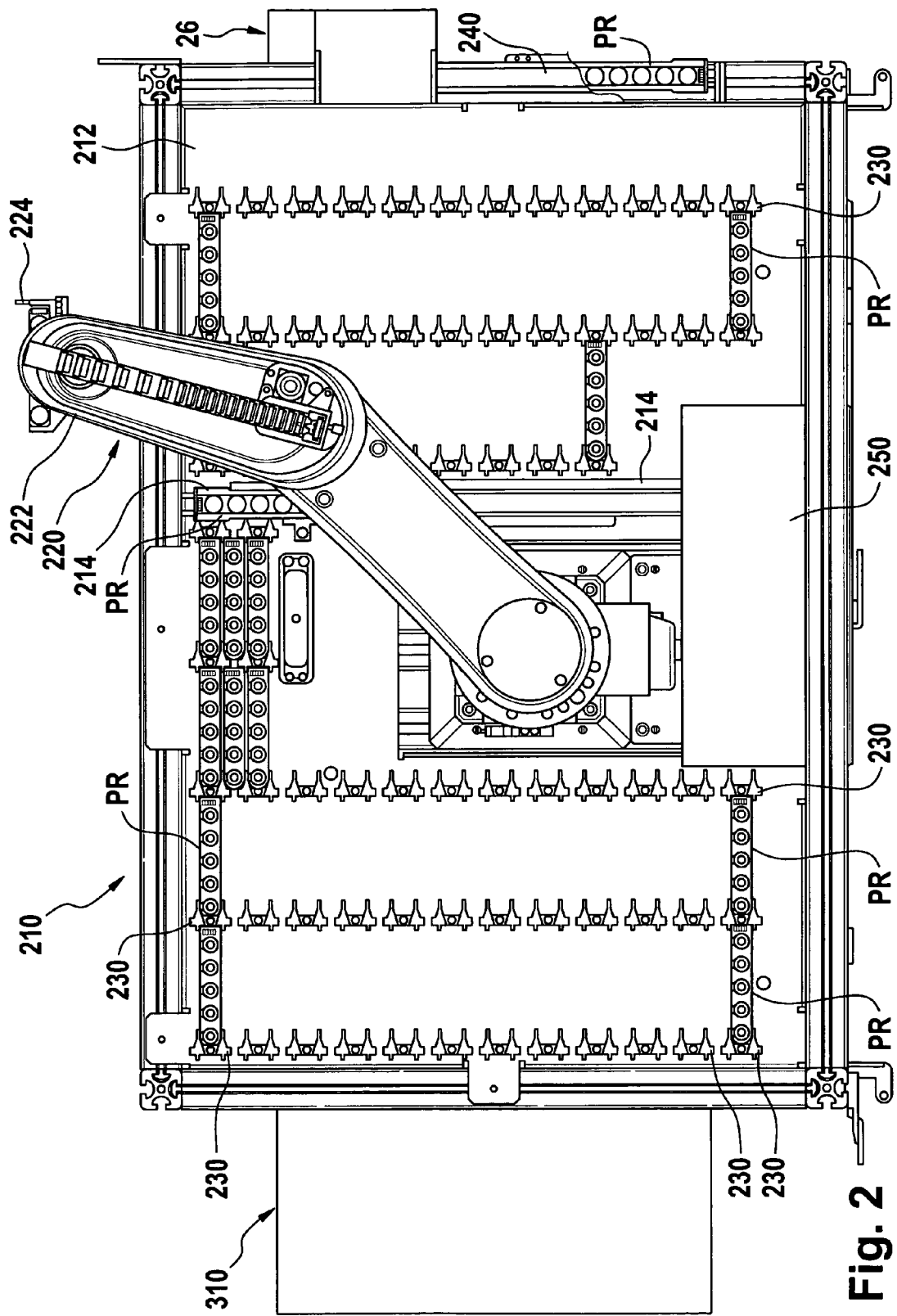
FIG. 2 shows a top view on a primary rack handler area of the laboratory system of the invention where incoming primary racks are handled.

FIG. 2 shows a top view of the primary rack handler area 210 of the laboratory system of the invention. The primary rack handler area 210 comprises a platform 212 inside the rack handler section 12 of FIG. 1. It further comprises a first robotic arm 220 which may be installed essentially in the centre of the platform 212 or at least at a position from which it can reach at least all locations within the primary rack handler area 210. Any known suitable robot can be used for this purpose, such as for example a SCARA robot with four axes and four degrees of freedom. The robotic arm 220 comprises, at its end, a gripper 222 designed to securely grip the racks to be handled.

On the platform 212, a conveyor 214 is provided for conveying incoming primary racks PR containing sample tubes (e.g., five sample tubes) to an image analyzing unit 250 which is also positioned on the platform 212.

Further, a plurality of alignment elements 230 are provided on the platform 212. The alignment elements 230 are designed to hold in place the primary racks PR in a desired alignment or orientation which corresponds to an orientation of the gripper 222 of the robotic arm 220. In order to ensure proper orientation of the primary racks PR in every step of processing (such that the sample tubes positions are always unambiguously identifiable), the primary racks may not be introduced directly on the conveyor 214 through the opening 20 but rather be taken up by the gripper 222 of robotic arm 220 and then placed on the conveyor 214. For this, a receiving position (not shown) for incoming racks is provided from which the robotic arm then takes up the incoming rack in order to place it onto the conveyor 214.

The conveyor 214 conveys the primary rack into the image analyzing unit 250 where the sample tubes in the primary rack are analyzed as to their geometry parameters. The determined geometry parameters of each sample tube are compared with predetermined geometry criteria and it is identified whether a sample tube is system conform or not. One of the geometry parameters to be analyzed is the presence of a cap on the sample tube, other parameters to be analyzed are for example the tube's diameter and height.

In case a sample tube is found to have no cap, the whole primary rack is sent to the capping station 26 before any other further processing. For this, the first robotic arm 220 places the primary rack onto the conveyor 240 conveying the primary rack with its sample tubes into the capping station 26 for a re-capping of the sample tube(s) identified to have no cap. After successful re-capping of the sample tube(s), the primary rack is brought back into the regular processing as explained in more detail below. Alternatively, as the case may be, the primary rack can be transferred back into the image analyzing unit 250 in order to make sure that now all sample tubes carry a cap and are fit for further processing.

Figure 3:
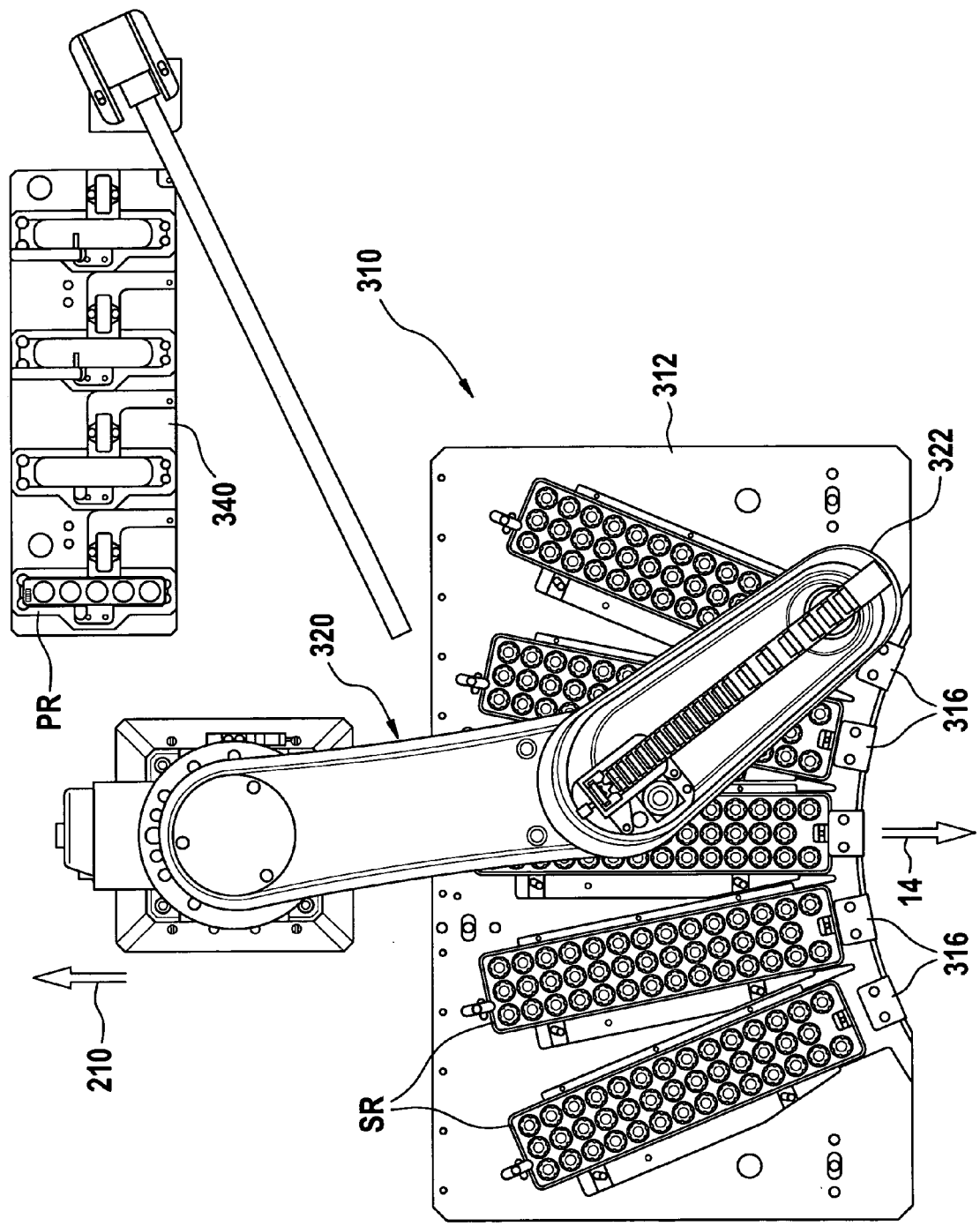
FIG. 3 shows a top view of the resorting station of FIG. 1.

FIG. 3 shows a top view of a resorting station 310 according to the invention. The resorting station 310 is also a part of the rack handler section 12 and is positioned adjacent to the primary rack handler area 210 of FIG. 2. For example, the resorting station 310 may be positioned on the left hand side of the primary rack handler area 210 in the depiction of FIG. 2, as indicated by reference numeral 310 in FIG. 2.

The resorting station 310 comprises a storage rack docking element 312 which is designed to receive a plurality of storage racks SR. The storage rack docking element 312 has basically the form of a substantially rectangular plate with a number of recesses 314 (five recesses in the embodiment shown in the drawings) adapted to fittingly receive according storage racks SR (cf., FIG. 4).

The resorting station 310 further comprises a second robotic arm 320 which is positioned behind the storage rack docking element 312 in such a manner that a gripper 322 attached to the second robotic arm 320 may be able to reach any location within the resorting station 310. The second robotic arm 320 is of similar or identical type as the first robotic arm 220 of the primary rack handler area 210 as described above but is provided with a different gripper 322, namely a sample tube gripper whereas the first robotic arm 220 of the primary rack handler area 210 is provided with a primary rack gripper 222.

Further, the resorting station 310 comprises a primary rack docking element 340 which is located at a position very close to the primary rack handler area 210 so as to be easily reachable by the first robotic arm 220 of the primary rack handler area 210 in order to be loaded with primary racks. In the illustration of FIG. 3, arrows with reference numerals 14 and 210, respectively, indicate the orientation of the resorting station 310, i.e. the primary rack docking element 340 and the back side of the second robotic arm 320 of the resorting station 310 are oriented towards the primary rack handler area 210 whereas the storage rack docking element 312 and the front side of the second robotic arm 320 are oriented towards the refrigerating or storage section 14.

In operation, a primary rack PR containing sample tubes S is conveyed into the image analyzing unit 250 by means of conveyor 214 where the sample tubes S are analyzed as to given predetermined geometric parameters in order to determine whether a sample tube is system conform or non-system conform. After this analysis, the primary rack PR is transferred, by means of the first robotic arm 220 of the primary rack handler area 210, to the primary rack docking element 340 (assuming that all sample tubes in the primary rack where found to carry a cap; otherwise there would first follow the re-capping procedure as described above, followed by another image analysis as the case may be).

When a primary rack PR is positioned in the primary rack docking element 340 of the resorting station, the second robotic arm 320 of the resorting station 310 starts unloading the sample tubes S contained in primary rack PR by taking them up subsequently with its tube gripper 322. The tube gripper 322 takes up a single sample tube S and moves it towards the storage rack docking element 312. On its way there, the sample tube S passes a barcode reader (not shown) which is positioned in front of the second robotic arm 320 in such a manner that the second robotic arm 320 may move the sample tube S, on its way to the storage racks SR, along the optical path of the barcode reader, at the same time rotating the sample tube slowly so that the barcode applied to the outer surface of the sample tube can be read by the barcode reader.

As all electronic elements of the laboratory equipment unit 10, namely the robotic arms and their respective control units, the image analyzing unit, the barcode readers, etc., are connected to a central CPU with a database, the second robotic arm 320 "knows" which sample tube in the primary rack about to be unloaded is system conform and thus is to be unloaded. Therefore, only sample tubes which where categorized before as system conform will be unloaded in the resorting section 310 while the sample tubes which where categorized as non-system conform will remain in the primary rack.

By means of the barcode reader of the resorting section 310, the system double checks if the sample tube held by the tube gripper 322 is system conform and retrieves the data necessary for resorting, e.g. the sample tube's diameter and/ or the sample tube's shelf life. These may be the two main parameters for resorting. Accordingly, a plurality of storage racks SR is provided on the storage rack docking element 312 with various diameter openings for receiving sample tubes from the second robotic arm 320. This means, that all sample tubes with a given diameter are correspondingly put in an appropriate storage rack, and that only sample tubes with the same shelf life are put into the same storage rack. Other sorting criteria are, of course, possible, such as, e.g., tube height.

Figure 4:
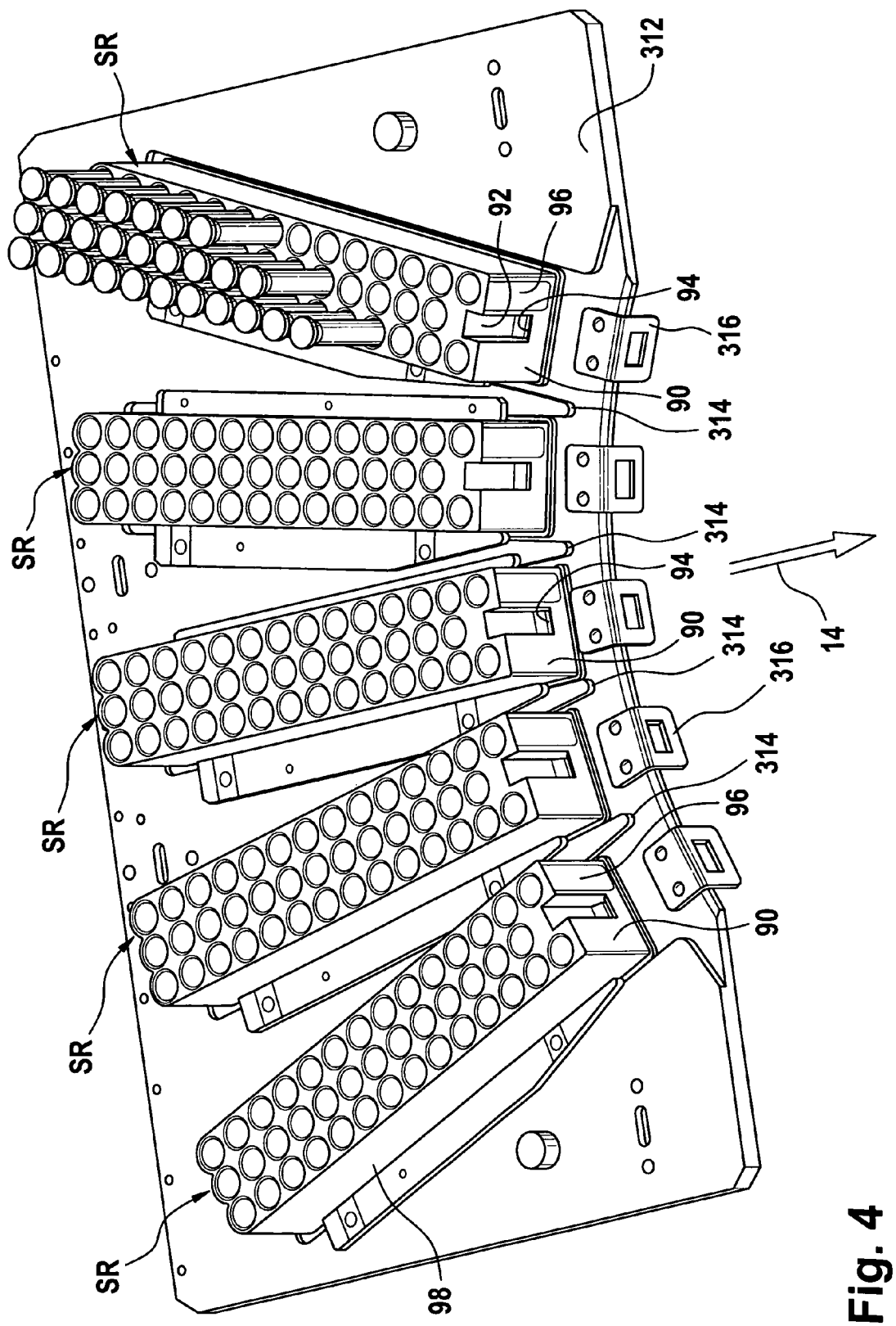
FIG. 4 shows a top perspective view of a storage rack docking element of the resorting station of FIG. 3.
Figure 9:
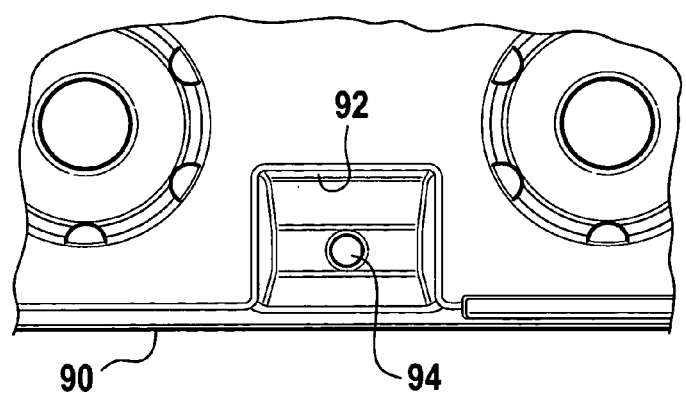
FIG. 9 shows an enlarged detail of the storage rack of FIG. 8.

As can be seen from both, FIGS. 3 and 4, the storage racks SR are not positioned in parallel to each other, but along a circle segment and pointing towards the gate (not shown) leading to the refrigerating or storage section 14 (i.e., the loading/unloading interface between the two sections 12, 14). When a storage rack is ready to be transferred into the refrigerator 16 of the storage section 14, the gate opens and a (third) robotic transfer system (cf., FIGS. 5 and 6) which is positioned within the refrigerator 16 extends through the gate opening and takes up the according storage rack in order to transfer it into the refrigerator. A front surface 90 of each storage rack SR comprises a vertical slot 92, at the lower end of which a substantially horizontal circular opening 94 is provided (cf., FIGS. 7 to 9). The third robotic transfer system may couple with the storage rack by engaging into the circular opening 94 with an appropriate complementary element, e.g., a hook 526 with appropriate dimensions, and draw the storage rack onto a platform of the third robotic transfer system. Next to the vertical slot 92 on the front surface 90 of the storage rack SR is an area 91 destined to receive a barcode label.

As can be seen from FIG. 4, the storage rack docking element 312 is provided with a plurality of recesses for receiving the storage racks, the recesses having a tee slot cross-section in which the storage rack SR can slidingly engage with corresponding extensions 96 provided along the lower edges of its lateral faces 98. Further, the storage rack docking element 312 is provided with orientation and abutment elements 316 in front of each recess 314 to facilitate positioning of the robotic transfer system in front of the storage racks.

Figure 5:
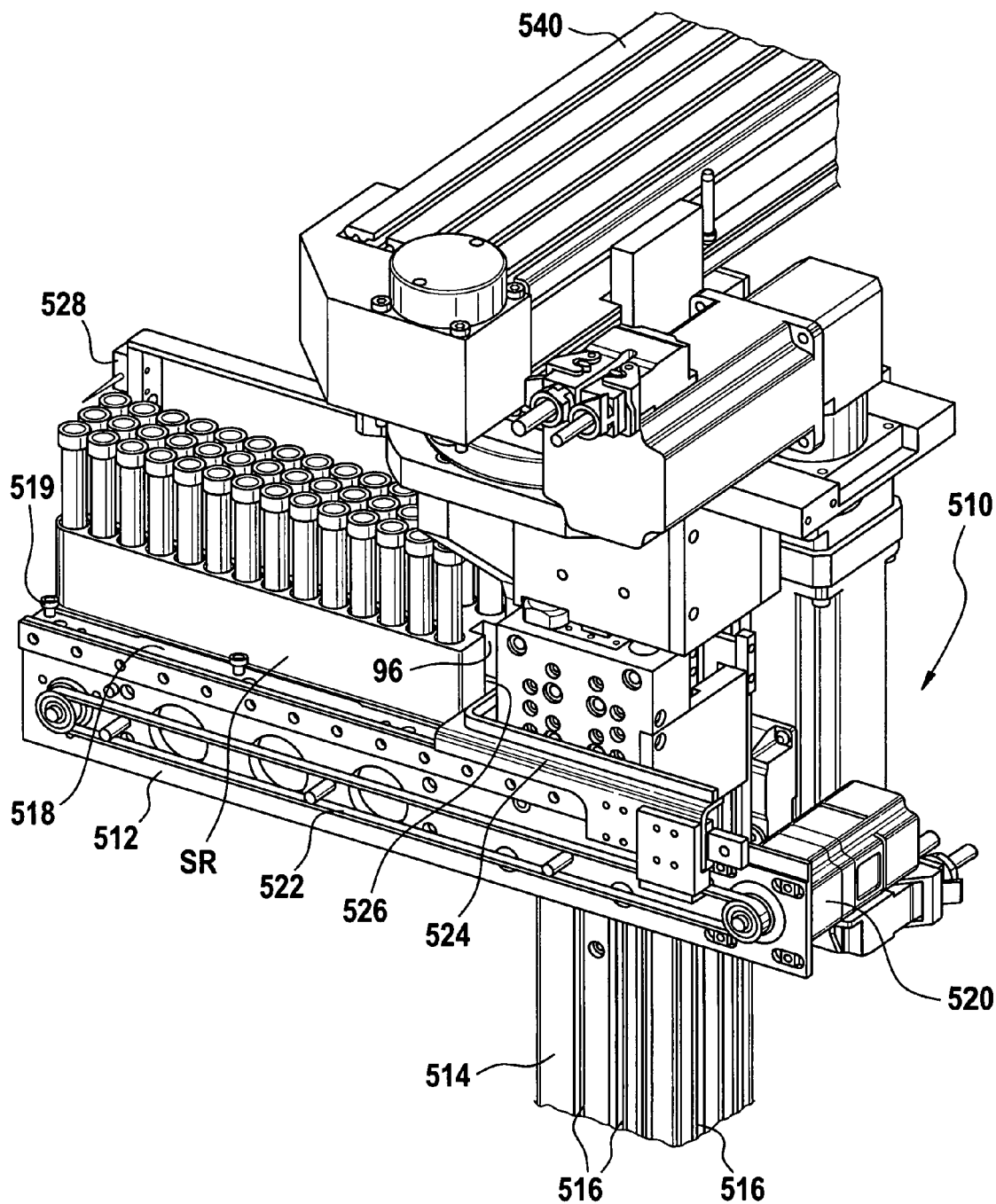
FIG. 5 shows a first perspective view of a robotic transfer system for handling storage racks.
Figure 6:
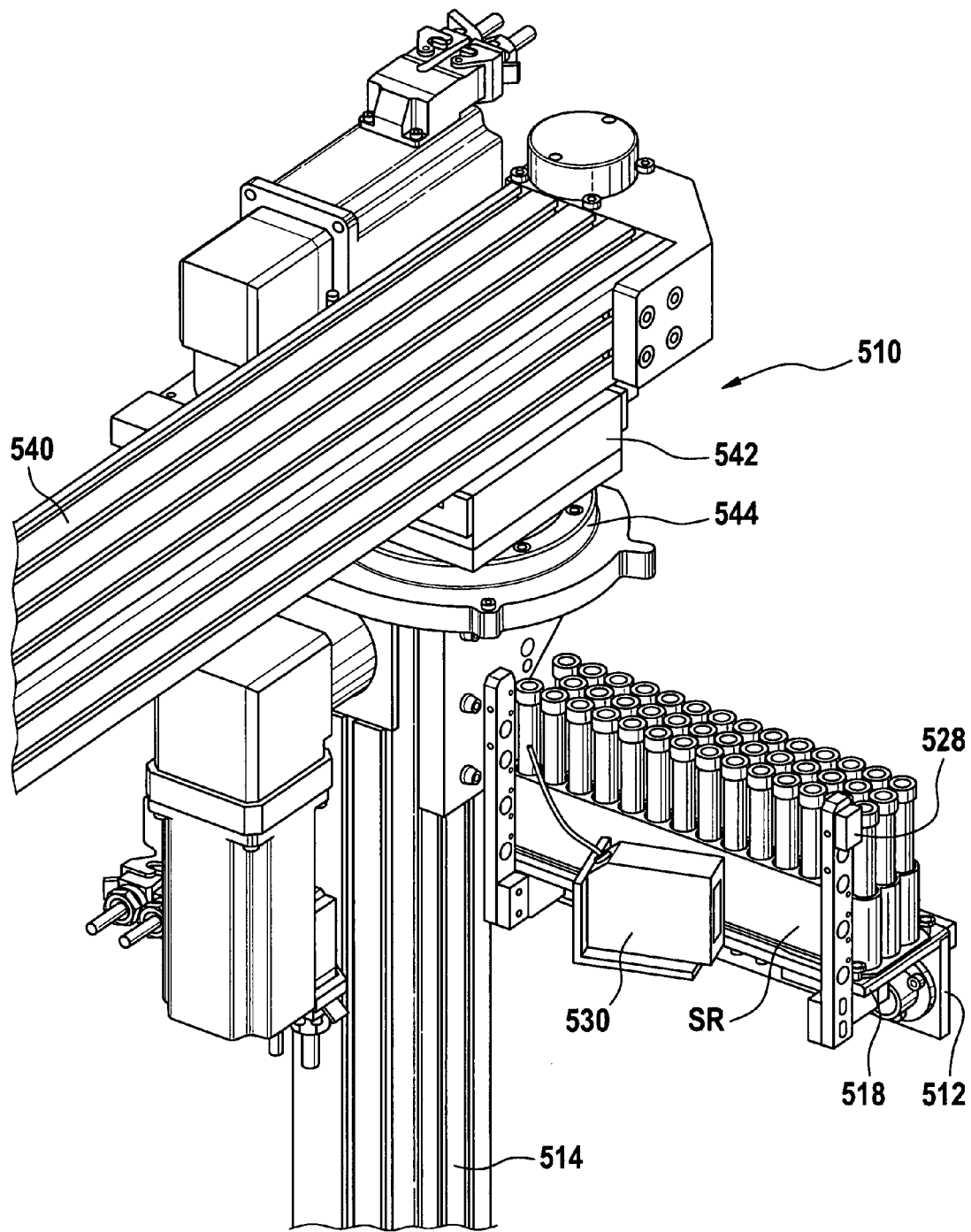
FIG. 6 shows a second perspective view of the robotic transfer system for handling storage racks of FIG. 5.
Figure 7:
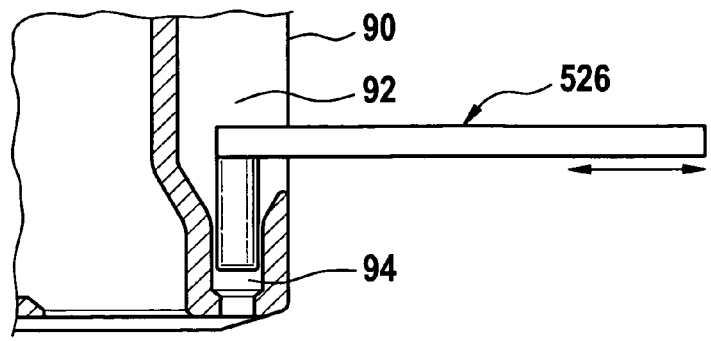
FIG. 7 shows an enlarged detail of a hook of the robotic transfer system for handling storage racks of FIG. 5 engaging with a storage rack.

With reference to FIGS. 5 and 6, a robotic transfer system 510 of the invention comprises a carrier element 512 with substantially vertical extension which can move along a vertical post 514 in longitudinal guide slots 516 by means of appropriate electric motors.

The carrier element 512 carries a platform 518 which can project forward from carrier element 512 by means of an electric motor 520 and belt drive 522. The carrier element 512 further comprises a kit 524 which is slidingly positioned on the platform 518 and which, at its front, is provided with the hook-like element 526 for engagement with the corresponding horizontal opening 94 of a storage rack SR.

The robotic transfer system 510 further comprises a barcode reader 530 which is positioned in such a manner that it can read the barcode label applied to the barcode surface 91 of a storage rack SR when the carrier element 512 and platform 518 are positioned in front of the storage rack. To this end, the barcode reader 530 may be attached to the carrier element with a slight angle as shown in FIG. 6.

Further, the robotic transfer system 510 comprises a rail bar 540 on the underside of which the vertical post 514 is slidingly attached by means of a sled 542, the sled 542 being able to move along guide slots of rail bar 540. The rail bar 540 may be attached to a ceiling of the refrigerator 16 so that an overhead movement of the robotic transfer system 510 is possible, with the advantage that the floor of the refrigerator along the aisle between the shelves remains free from any guide bars or rails. The refrigerator may be provided with suitable sensors so that when a person enters the refrigerator the robotic transfer system comes to a standstill or first moves to a neutral or home position, e.g., at the opposite aisle end from the door, where it then comes to a standstill. The sensors might be connected to the door (such as a safety switching circuit) and/or to the floor area (such as a light barrier, any other photosensitive relay, a step sensor which senses weight on the floor, etc.).

The vertical post 514 of the robotic transfer system 510 is attached to the sled 542 by means of a rotary joint 544 which enables full rotary movement of the post 514 together with the carrier element 512.

Figure 10:
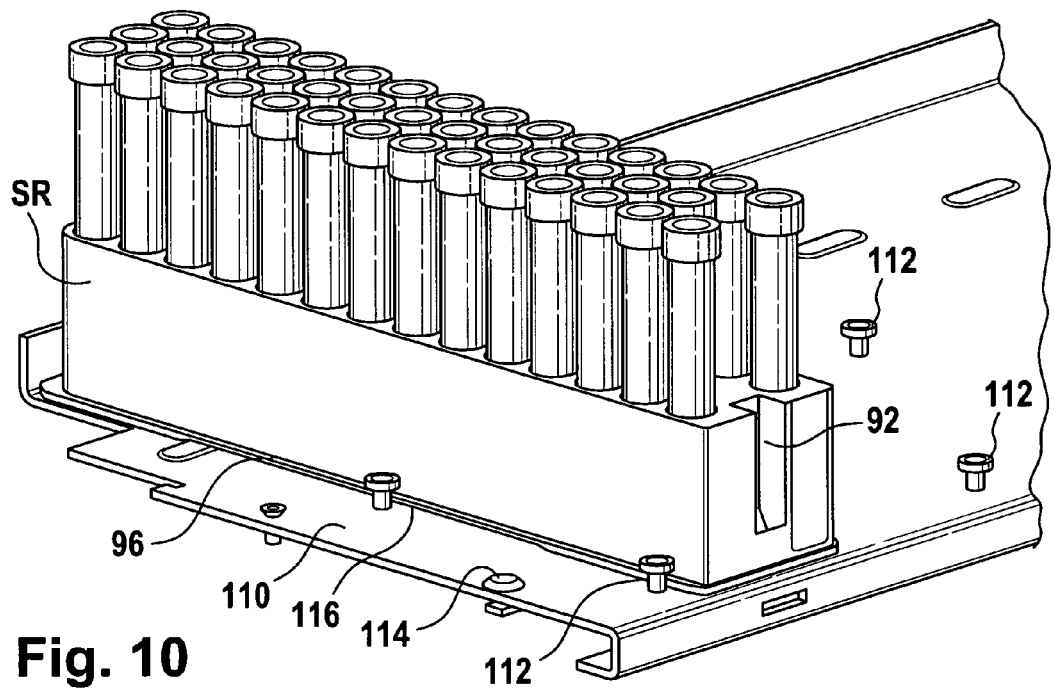
FIG. 10 is a perspective view of a storage rack on a storage shelf in the storage unit of FIG. 1.
Figure 11:
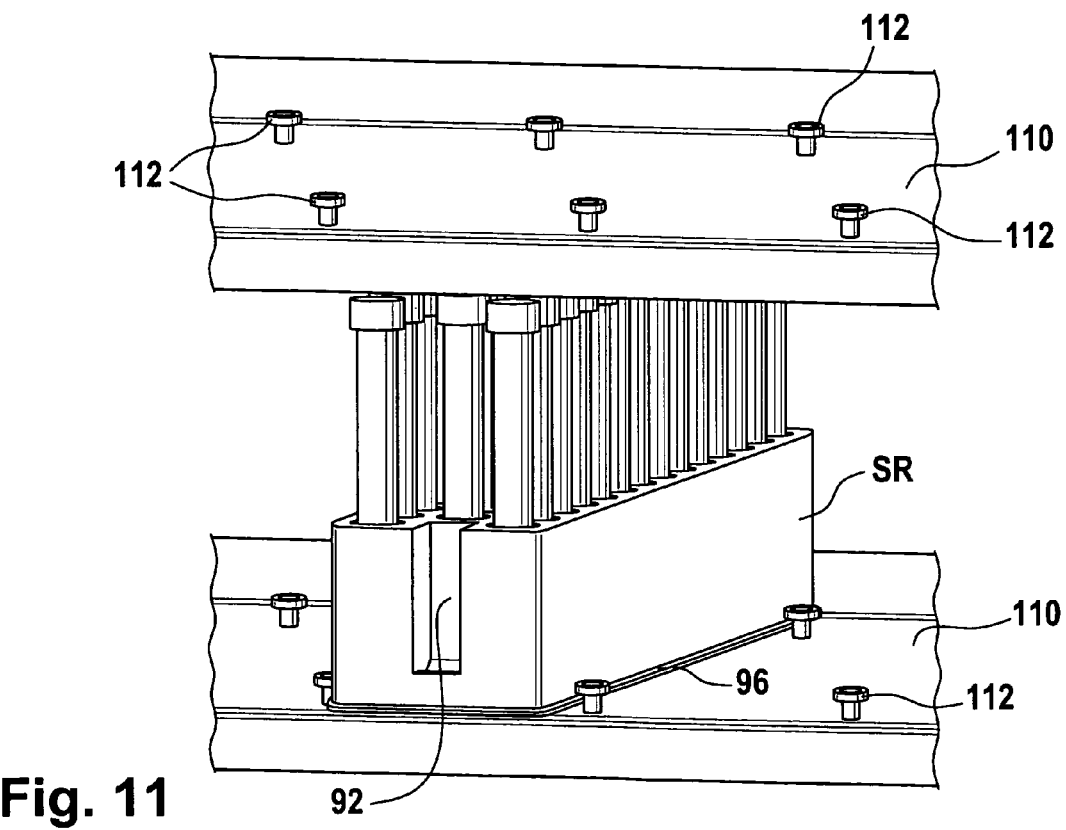
FIG. 11 is another perspective view of a storage rack between two shelves.

FIGS. 10 and 11 show perspective views of a storage rack SR in storage position on a shelf 110. Each shelf 110 comprises a plurality of T-pins 112 which are aligned on the shelves 110 so as to form a receiving compartment for a storage rack SR. The distance between two pins 212 in longitudinal direction of a shelf 110 may be about equal to the width of the storage rack SR at its bottom side including the longitudinal extensions 96. In loading direction, there should be at least two pins 112 in order to provide a proper guiding of the storage rack SR when slid onto the shelf. A pin 112 may be provided at about half length of a storage rack and/or at the rear side of the shelf (cf., FIGS. 10 and 11, respectively). The T-shape of the pins 112 ensures a fitting position of the storage rack SR on the shelf as the longitudinal extensions 96 are positioned below the heads of the T-shaped pins, encompassing so-to-say underneath the heads of the T-shaped pins, and thus the racks can only be moved in one direction.

Further, the shelves 110 may comprise elevated retaining elements 114 indicated in FIG. 10. The retaining elements 114 are typically located in the back area of each shelf 110 and are designed to fit underneath a corresponding recess 116 of the storage rack SR. The elevated retaining element 114 may be formed by a stamping of the sheet metal of the shelf or any other appropriate method. Although it may be possible to form the retaining element on the shelf by fixing it thereto (such as glueing, screwing, welding), it should be advantageous to make it in one piece with the shelf for robustness reasons. The recess 116 at the bottom side of the storage rack SR may have a concave form to better fit with the elevated retaining element 114. The retaining element 114 has the function to retain the fully inserted storage rack in its storage position, thus preventing the storage rack, e.g., to slowly move away from the storage position and possibly fall, due to, e.g., vibrations during operation of the system. Such elevated retaining elements 114 may, of course, also be provided in the recesses 314 of the storage rack docking element 312.

The platform 518 is connected with a height adjustment device, typically together with the carrier element 512. The height adjustment device lowers the platform slightly with regard to the level of the shelf from which a storage rack is to be pulled just before the storage rack is pulled onto the platform in order to avoid that the storage rack might get stuck at the front edge of the platform 518 when being pulled from the shelf onto the platform. In case a storage rack is to be pushed from the platform onto the shelf, the height adjustment device raises the platform slightly with regard to the level of the shelf for the same reason, i.e., in order to avoid that the platform might get stuck with its front edge when being pushed over the front edge of the shelf.

In the initial operation phase, the program of the CPU controlling the robotic transfer system 510 runs a self-teaching routine. This self-teaching routine works by means of a sensor reading markings along the shelves, e.g. applied to each of the respective top shelf storage rack end positions and bottom shelf storage rack end positions and with the information of how many storage positions per shelf and how many shelves (i.e., rows of shelves) one shelf wall of the storage section comprises. The self-teaching routine allows the robotic transfer system 510 to gauge itself by having the robotic transfer system 510 move to a first storage rack end position of either the top or the bottom shelves, then move horizontally along the shelf until it identifies the respective opposing storage rack end position, all by measuring the distance between the two storage rack end positions. Then, the robotic transfer system 510 moves vertically to the respective opposing bottom or top shelf until it identifies the third storage rack end position, again by measuring the distance between the two storage rack end positions. Then, the robotic transfer system 510 moves again horizontally along the shelf to the fourth storage rack end position, again measuring the distance between these two storage rack end positions. To make it complete, the robotic transfer system 510 may optionally move again vertically to the initial storage rack end position to obtain a fourth measured distance. Of course, the order of the movement is not critically important, for example the robotic transfer system 510 may also first move vertically before moving horizontally. The described self-teaching routine can be done on the basis of, e.g., four markings, i.e., one marking per storage rack end position.

Gauging is then obtained by calculating the distances between individual storage positions by dividing the distance between horizontal storage rack end positions by the number of storage rack positions and by dividing the distance between vertical storage rack end positions by the number of shelves and by storing the absolute coordinates of the four storage rack end positions. On the basis of these figures, the robotic transfer system 510 may find every shelf storage position with its internal coordinate system. A similar self-teaching routine is executed also with respect to the storage rack docking element 312 shown in FIG. 4, when a storage rack SR has to be stored or retrieved, wherein the abutment elements 316 have the function of markings located in front of each recess 314.

Figure 12:
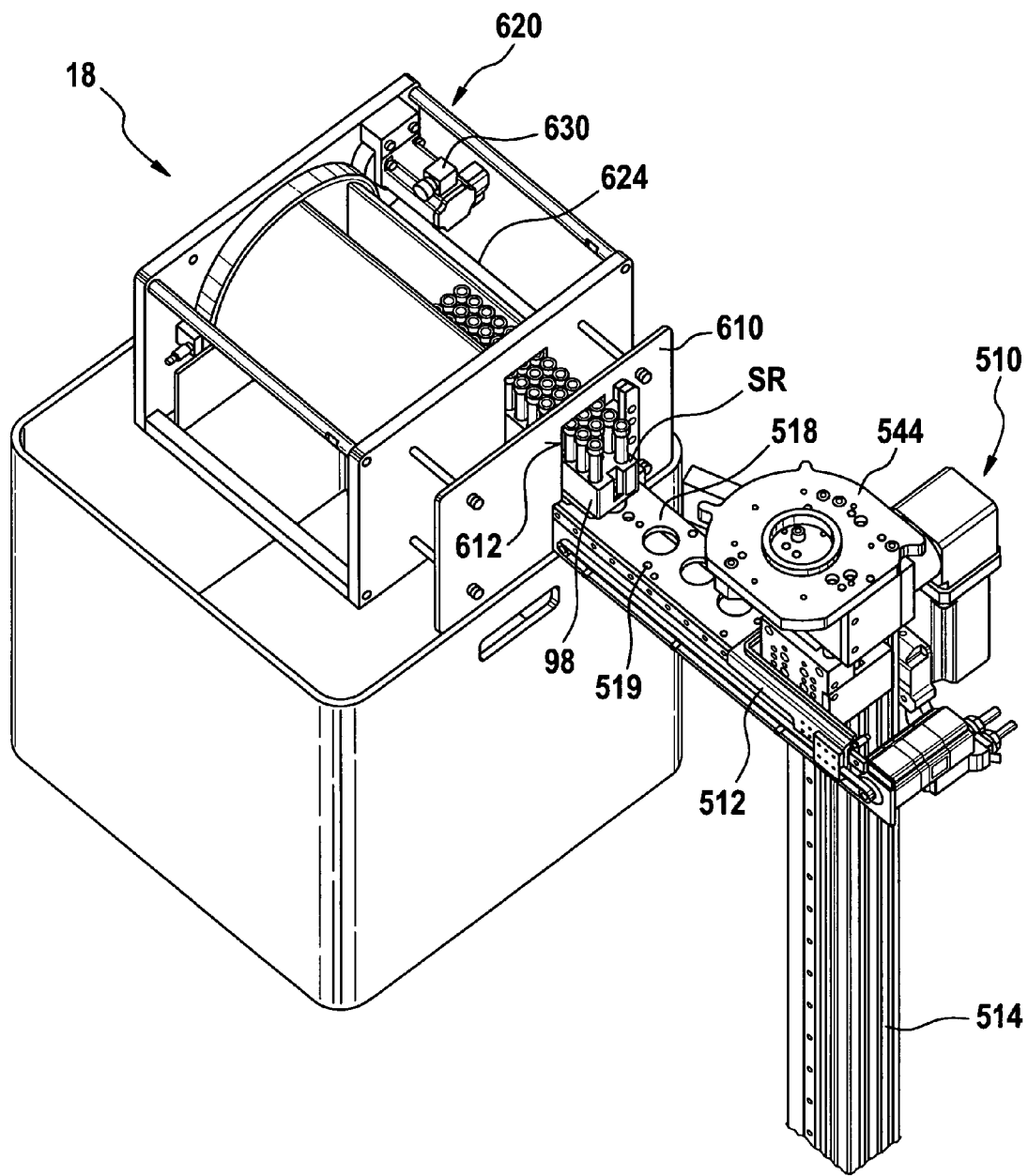
FIG. 12 is a perspective top view of a disposal unit and the robotic transfer system of FIG. 5.

FIG. 12 shows a schematic perspective view of the disposal unit 18 which is a part of the storage section 14, being located outside of the refrigerator 16 but adjacent to the refrigerator 16. The refrigerator 16 and the disposal unit 18 are separated by a partition wall 610 (only a portion of which is shown in FIG. 12) which is provided with a gate opening 612 large enough for a fully loaded storage rack to pass through.

The disposal unit 18 comprises a tilt module 620 which may be fixedly attached to the partition wall 610 in alignment with the gate opening 612. Attachment may be done for example by means of bolts and nuts with appropriate dimensions (cf., FIG. 12). Underneath the tilt module 620, there is provided a waste container 640. The tilt module comprises a storage rack park position 622. The rack park position 622 may be a platform with guide elements with a T- or L-shaped cross-section for holding the storage rack SR in position when the storage rack SR is tilted over in the tilt module 620. The guide elements may be guide grooves formed by raised side edges, encompassing the lower edges of a storage rack when being slid in the park position so that the protruding extensions 96 provided along longitudinal edges of the storage rack engage with the raised edges guide grooves of the platform 622. Alternatively, instead of guide grooves the platform 622 may comprise, as guide elements, T-shaped guide pins 112 as described above in connection with the shelves 110 of the storage section 14.

The rack park position 622 is provided within a drum 624 which is rotatable around a centre axis 626.

In operation, a storage rack SR is pushed into the drum 624 in the rack park position 622 by means of the robotic transfer system 510 of the refrigerator 16 through the gate opening 612 in the partition wall 610 between refrigerator 16 and disposal unit 18. Once the storage rack SR is in place and the gate opening 612 is closed, the drum 624 rotates about the rotation axis 626, e.g., counter-clockwise as shown in FIGS. 13A, 13B and 13C so that the storage rack module held in place in the rack park position 622 by the above-described guide grooves is tilted over and the sample tubes S contained therein fall, due to gravity, in the waste container 640 provided below the tilt module 620.

As alternative to the tilt module 620 the robotic transfer system 510 of the refrigerator 16 may be adapted (not shown) to extend through the gate opening 612 in the partition wall 610 between refrigerator 16 and disposal unit 18 and to rotate about a rotation axis so that the storage rack module is held in place and the sample tubes S contained therein fall, due to gravity, in the waste container 640 provided underneath.

Thus, in one aspect a method of handling sample tube racks comprises the steps of loading sample tube racks (e.g., storage racks SR) into the storage section (14) through a gate by means of the robotic transfer system (510), of retrieving, upon need or after a certain time period, e.g., shelf life, has elapsed, a rack from the storing section (14) through a gate by means of the robotic transfer system (510), in case the certain storage time period has lapsed, bringing a rack into the disposal unit (18) by means of the robotic transfer system (510), and disposing sample tubes through the disposal unit (18).

Figure 13B:
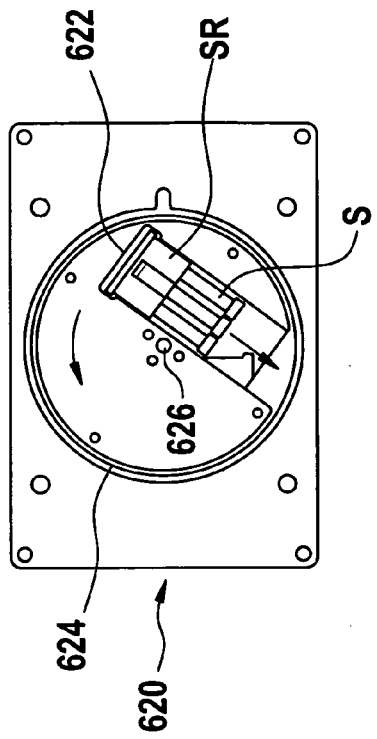
FIGS. 13A to 13C show front views of a drum of the disposal unit of FIG. 12 in subsequent operation steps.
Figure 13C:
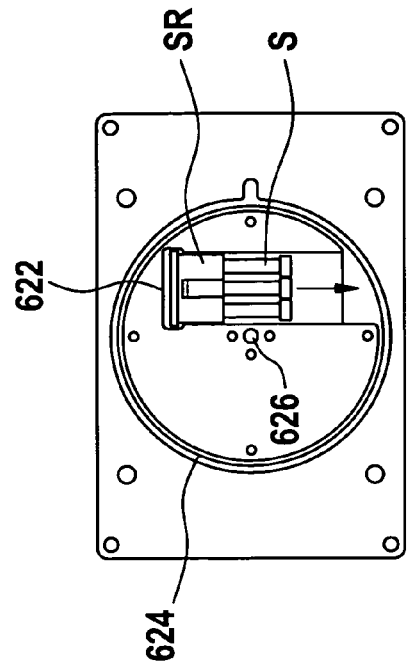
Figure 13A:
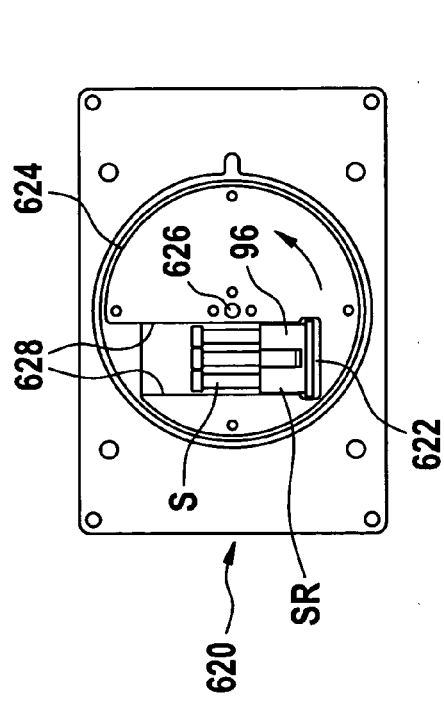
Figure 13A:
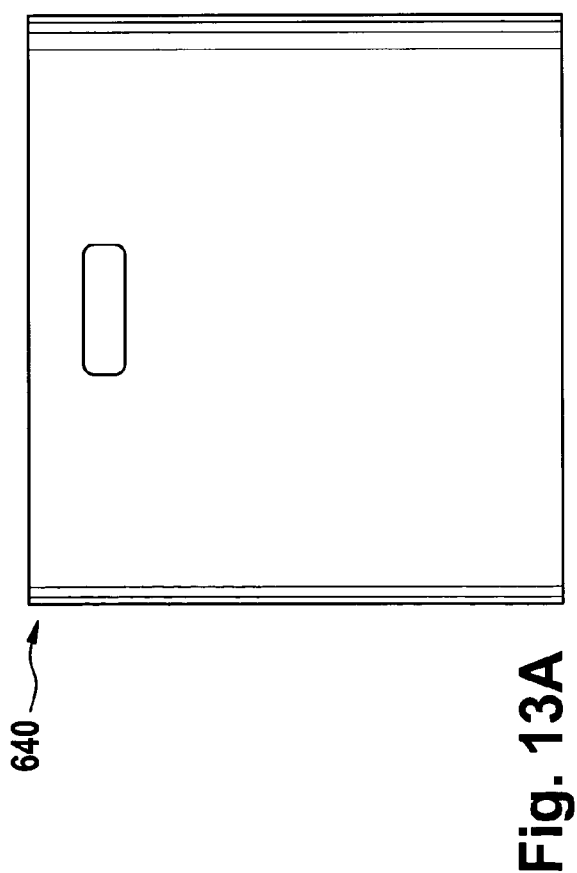

As may be seen from FIGS. 13A to 13C, the rack park position 622 is located off-centre from the rotation axis 626 which makes that the storage rack SR itself is not rotated but rather tilted so that the process of turning over the storage rack SR is smoothened so that the sample tubes preferably slide out of the storage rack rather than fall out of the same. This effect is intensified by the presence of two side walls 628 within the drums 624 which extend adjacent to the side walls 98 of the storage rack SR beyond the height of the tubes S. As an effect, the sample tubes S fall or, more preferably slide out of the drums 624 in a controlled manner so that the likelihood of a sample tube dropping outside of the waste container 640 is ruled out or at least minimised.

Figure 14:
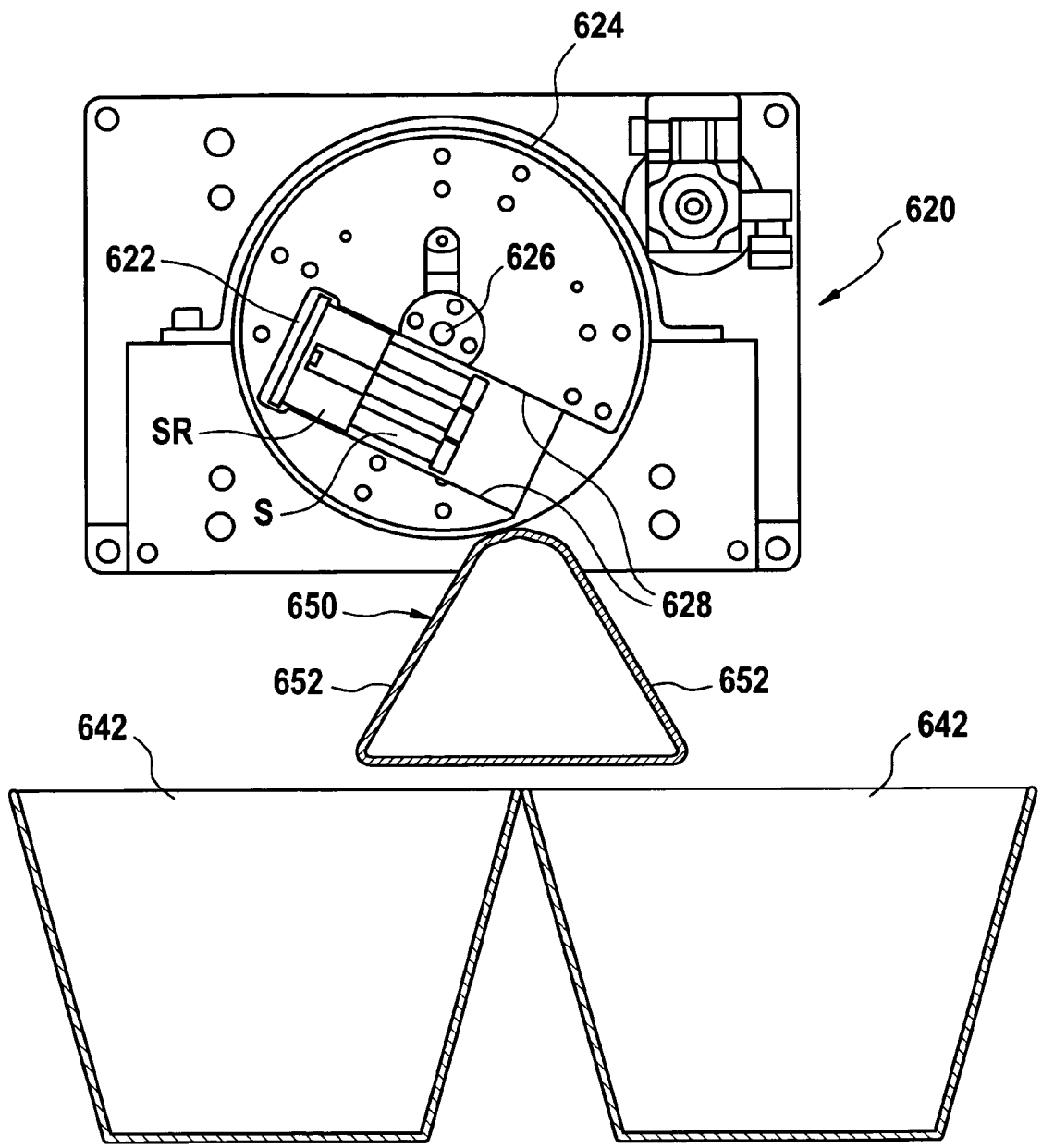
FIG. 14 shows another embodiment of the disposal unit of FIG. 12.

FIG. 14 shows an alternative embodiment of the disposal unit. This embodiment comprises two smaller waste containers 642. The tilt module 620 remains unchanged compared to the embodiment shown in FIG. 13 (merely the rack park position 622 is located on the other side of the rotation axes 626 in a mirror-inverted manner).

Underneath the tilt module 620 between the drum 624 and the two waste containers 642, a deflector 650 is provided. The deflector 650 has a cross-section of substantially triangular form (which makes it some kind of double deflector with two downwardly sloped deflector plates 652) and is positioned with its mid-perpendicular plane vertically above the adjacent edges of the two waste containers 642 touching each other. The positioning of the triangular deflector 650 is such that, when the drum 624 is rotated in either direction, the sample tubes S falling or sliding out of the storage rack SR first slide along the side walls 628 and then along either one of the two sloped plates 652 of the deflector 650 into the respective waste container 642 as the triangular cross-section is sloped towards the upper openings of the waste containers. The double deflector 650 therefore prevents sample tubes S from falling in between the two waste containers 642 or from hitting the edges of the waste containers 642 placed below the drum 624 which could make them rebound and fall next to the waste containers.

Additionally, a sensor (not shown) may be provided in order to detect when the waste container is full and should be changed. This sensor might be connected to a control unit or CPU (not shown) of the tilt module in order to disrupt operation of the tilt module until the waste container is emptied or replaced in order to prevent sample tubes overflowing and samples being spilled. Another sensor may be also provided to check that the functioning of the drum 624, e.g., angle of rotation, receiving position, etc., are correct.

Following disposal, the emptied storage rack is withdrawn from the disposal unit 18 by the robotic transfer system 510. During retraction, a sensor 528 located on the robotic transfer system 510 may detect whether any tube has remained in the storage rack SR. If this is the case, a non-conform status is detected and the storage rack SR is, e.g., transported to a park position, e.g., on one of the upper shelves 110 of the storage section 14 where more space in height is allocated, before further processing. The same or another sensor may have also the function of height sensor, e.g., to check during the operation of storing a storage rack that the height of the tubes does not exceed a certain threshold value, e.g., given by the distance between two shelves of the refrigerator 16. Alternatively, the storage rack is transported to a storage rack docking element 312 of the resorting section 310. Here, the sample tubes (S) remained in the storage rack are resorted to a different rack, e.g. a waste rack (WR), which preferably comprises larger diameter openings, typically larger than the diameter of any tube handled by the system, e.g., 2-3 cm diameter or more. Afterwards, the waste rack (WR) is transported by the robotic transfer system 510 to the disposal unit 18 and the disposal procedure is repeated. The above process may be repeated more times if necessary. Normally, the use of larger diameter openings in the waste rack (WR) reduces the risk that this occurs.

Thus the method of handling sample tube racks may comprise the steps of sensing by means of a sensor 528 whether sample tubes (S) have remained in the sample tube rack after disposing and in the affirmative transporting the rack to a park position and/or resorting the remained sample tubes (S) to a waste rack (WR) and repeating the disposal procedure.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A laboratory system to handle laboratory sample tube racks, comprising:
   a storage section (14) with a plurality of shelves (110) for storing a plurality of sample tube racks,
   wherein the storage section further comprises:
   a) a disposal unit (18) for disposing sample tubes from the sample tube racks; and
   b) a robotic transfer system (510) configured for loading the sample tube racks into the storage section (14), for retrieving the sample tube racks from the storing section (14) and for bringing a sample tube rack to the disposal unit (18) after a given storage time of the sample tube rack has elapsed.

2. The laboratory system of claim 1, wherein the robotic transfer system (510) comprises a coupling element (526) for coupling with a sample tube rack to be conveyed, the coupling element (526) transferring push/pull forces on the sample tube rack when coupled thereto, and a platform (518) for carrying the sample tube rack to be conveyed, wherein the platform (518) is connected with a height adjustment device, the height adjustment device lowering the platform (518) with regard to shelf level in case a sample tube rack is pulled onto the platform (518), and the height adjustment device raising the platform (518) with regard to shelf level in case a sample tube rack is pushed from the platform (518).

3. The laboratory system of claim 2, wherein the coupling element (526) is an L-shaped hook for engagement with a corresponding opening (94) of a sample tube rack.

4. The laboratory system of claim 1 wherein the storage section comprises one or more shelves, and wherein each shelf (110) of the one or more shelves comprises a plurality of T-pins (112) which are aligned on the shelves (110) so as to form a receiving compartment for a sample tube rack and provide a proper guiding of the sample tube rack when slid onto the shelf (110).

5. The laboratory system of claim 4, wherein the shelves further comprise a plurality of elevated retaining elements (114) for retaining a fully inserted sample tube rack in its storage position.

6. The laboratory system of claim 1, wherein the disposal unit (18) comprises a tilt module (620) and a waste container (640, 642), the tilt module having a rack park position (622) positioned above the waste container (640, 642), the tilt module (620) being designed to tilt a sample tube rack loaded by the robotic transfer system (510) into the rack park position (622) over such that sample tubes (S) contained in the sample tube rack fall or slide into the waste container (640, 642) below.

7. The laboratory system of claim 6, wherein the rack park position (622) comprises guide elements with a T- or L-shaped cross-section for holding the storage rack (SR) in position when the storage rack (SR) is tilted over in the tilt module (620).

8. The laboratory system of claim 6, further comprising a deflector (650) wherein the deflector is positioned between the tilt module (620) and the waste container (640, 642) and guides falling sample tubes (S) into the waste container (640, 642).

9. The laboratory system of claim 1, further comprising a self-teaching system which enables the robotic transfer system (510) to gauge itself, the self-teaching system comprising markings at defined positions along the shelves (110).

10. The laboratory system of claim 1, wherein the robotic transfer system (110) further comprises a sensor (528) for sensing the presence and/or the height of sample tubes (S) in a storage rack (SR).

11. A method of operating a storage section (14) of a laboratory system, the storage section (14) comprising (a) a plurality of shelves (110) for storing a plurality of sample tube racks-, the shelves including a top shelf and a bottom shelf, the top and bottom shelves having a first end and an opposite second end and (b) a robotic transfer system (510) for loading sample tube racks into the storage section (14) through a gate and retrieving sample tube racks from the storing section (14), comprising the following steps:
   the robotic transfer system (510) moving to one of the top shelf or the bottom shelf;
   the robotic transfer system (510) moving to the first end of the top or bottom shelf and identifying, by means of a sensor, a first marking defining a first storage rack end position;
   the robotic transfer system (510) moving along the top or bottom shelf towards the opposite second end and identifying a second marking defining a second storage rack end position and measuring, by means of a sensor, the distance between the first and second storage rack end positions;

the robotic transfer system (510) moving vertically to the respective other one of the top shelf or the bottom shelf until it identifies a third marking defining a third storage rack end position and measuring, by means of a sensor, the distance between the second and third storage rack end positions;

the robotic transfer system (510) moving along the other one of the top shelf or the bottom shelf towards an opposing shelf end from the third storage rack end position and identifying a fourth marking defining a fourth storage rack end position and measuring, by means of a sensor, the distance between the third and fourth storage rack end positions;

calculating, in a CPU of the robotic transfer system (510), the distances between individual storage positions by dividing the measured distance between horizontal storage rack end positions by the number of storage rack positions and by dividing the distance between vertical storage rack end positions by the number of shelves; and storing the absolute coordinates of the four storage rack end positions.

12. A method to handle laboratory sample tube racks in a laboratory system comprising a storage section (14) having a plurality of shelves (110) for storing a plurality of sample tube racks, a disposal unit (18) and a robotic transfer system (510), the method comprising the steps of a) loading sample tube racks into the storage section (14) through a gate by means of the robotic transfer system (510);

b) retrieving upon need a sample tube rack from the storing section (14) through a gate by means of the robotic transfer system (510);

c) bringing a sample tube rack into the disposal unit (18) by means of the robotic transfer system (510) after a given storage time for the said sample tube rack has elapsed; and d) disposing sample tubes through the disposal unit (18).

13. The method according to claim 12 further comprising the steps of:

e) sensing by means of a sensor (528) whether sample tubes (S) have remained in the sample tube rack after disposing step (d) and in the affirmative, f) transporting the sample tube rack to a park position and/or resorting the remained sample tubes (S) to a sample tube storage rack and repeating steps c) and d).

* * * * *